United States Patent [19]
Stein

[11] Patent Number: 5,948,389
[45] Date of Patent: Sep. 7, 1999

[54] METHOD OF ENHANCING THE ANALGESIC EFFICACY OF LOCALLY AND TOPICALLY ADMINISTERED OPIOIDS AND OTHER LOCAL ANESTHETICS

[75] Inventor: Christoph Stein, Baltimore, Md.

[73] Assignee: El Khoury & Stein, Ltd., Long Beach, Calif.

[21] Appl. No.: 08/922,573

[22] Filed: Sep. 3, 1997

Related U.S. Application Data

[63] Continuation of application No. 08/488,021, Jun. 7, 1995, abandoned.

[51] Int. Cl.[6] ...................................................... A61K 9/10
[52] U.S. Cl. ........................... 424/45; 424/443; 424/680; 514/816; 514/817; 514/818; 514/887; 514/944; 514/938; 514/947
[58] Field of Search .................................... 424/45, 78.05, 424/443, 451, 464, 680; 514/816, 817, 818, 886, 937, 887, 944, 938, 947

[56] References Cited

PUBLICATIONS

European Journal of Pharmacology, 155 (1988) 255–264 "Antinociceptive effects of $\mu$– and k–agonists in inflammation are enhanced by a peripheral opioid receptor–specific mechanism."

Neuroscience Letters, 84 (1988) 255–228 "Peripheral effect of fentanyl upon nociception in inflamed tissue of the rat."

The Journal of Pharmacology and Experimental Therapeutics, vol. 248, No.3, pp. 1269–1275 (1989) by The American Society for Pharmacology and Experimental Therapeutics. "Pheripheral Opioid Receptors Mediating Antinociception in Inflammation. Evidence for Involvement of Mu, Delta and Kappa Receptors."

Proc. Natl. Acad. Sci. USA, vol. 87, pp. 5935–5939, Aug. 1990, "Opioids from immunocytes interact with receptors on sensory nerves to inhibit nociception in Inflammation."

The Journal of Neuroscience, Apr. 1990 10(4): 1292–1298, "Intrinsic Mechanisms of Antiociception in Inflammation: Local Opiod Receptors and $\beta$–Edorphin."

The New England Journal of Medicine 325:1123–1126 (Oct. 17, 1991). "Analgesic Effect of Intraarticular Morphine After Arthroscopic Knee Surgery."

Anesthesiology 77:263–266, (1992). "Intraarticular Morphine, Bupivacaine, and Morphine/Bupivacaine for Pain control after Knee Videoarthroscopy."

The Lancet—vol. 342, Aug. 7, 1993, pp. 320–324 "Local analgesic effect of endogenous opioid peptides."

Anesth Analg 1993;76:182–91, "Peripheral Mechanisms of Opioid Analgesia."

Critical Review in Neurobiology, vol. 5, Issue 3 (1990), pp. 265–311. "Microenvironment of the Peripheral Nervous System Under Normal and Pathological Conditions."

Current Opinion in Anaesthesiology (1994) 7:347–351. "Pheripheral and non–neuronal opioid effects."

The Journal of Neuroscience, Jan. 1995, 15(1): 165–172. "Perineurial Defect and Peripheral Opioid Analgesia in Inflammation."

Pharmacology Biochemistry & Behavior, Vo. 31, pp. 445–451 (1988). "Unilateral Inflammation of the Hindpaw in Rats as a Model of Prolonged Noxious Stimulation: Alterations in Behavior and Nociceptive Thresholds."

Current Opinion in Anaesthesiology (1993), 6:400–408. "Small–volume resuscitation."

Thorstud, G.K. Pleural reactions to irritants. Acta Chir. Scaud. 1965; 355. Supp:1–74.

Agon et al. (1988). *J. Pharm. Pharmacol.* 40(8):539–43.

*Primary Examiner*—Raj Bawa
*Attorney, Agent, or Firm*—Armstrong, Westerman, Hattori, McLeland & Naughton

[57] ABSTRACT

The present invention is a method for enhancing the analgesic efficacy of a locally applied opioid analgesic or local anesthetic agent in a mammal having an impermeable perineurium barrier sheet about the peripheral sensory nerves at the site of action of the analgesic or anesthetic agent. The method involves applying to that site an effective amount of the analgesic or anesthetic agent dissolved in a hyperosmolar solution having an osmolality of above 300 mOsm/l.

12 Claims, 5 Drawing Sheets

METHOD OF ENHANCING THE ANALGESIC EFFICACY OF LOCALLY AND TOPICALLY ADMINISTERED OPIOIDS AND OTHER LOCAL ANESTHETICS

This application is a continuation of application Ser. No. 08/488,021 filed Jun. 7, 1995, now abandoned.

FIELD OF THE INVENTION

The present invention is directed to the method for improving the efficacy of opioid analgesics and other local anesthetics acting on peripheral nerves to inhibit pain without the migration of the opioid or local anesthetic into the bloodstream comprising administering a composition comprising dilute solutions of opioid analgesics and other local anesthetics in combination with hyperosmolar solutions.

BACKGROUND OF THE INVENTION

Opioid drugs are potent analgesics which exert their effects by activating opioid receptors within and/or outside the central nervous system. Opioid receptors have been demonstrated on sensory nerves in both inflamed and normal subcutaneous tissue.

It has been shown that when opioids are applied locally (i.e., intraplantarly) to circumscribed inflamed areas outside the central nervous system, they can produce analgesic effects by activating opioid receptors on peripheral sensory nerves. (Stein Eur. J. Pharm. 155:255–265 (1988); Stein et al., Neurosci. Lett., 84:225–228 (1988)). Importantly, such peripheral analgesic effects can be achieved with very low doses of opiates which do not reach the brain (i.e., do not cross the blood-brain barrier) and, therefore, do not produce the well known and serious central opioid side effects (e.g., somnolence, nausea, depression of breathing, dysphoria, addiction). This has been shown in a large number of controlled and published studies in animals (Stein et al., Neurosci. Lett., 84:225–228 (1988); Stein et al., Eur. J. Pharmacol., 155:255–264 (1988); Stein et al., J. Pharmacol. Exp. Ther., 248(3):1269–1275 (1989); Stein et al., Proc. Natl. Acad. Sci. USA, 87:5935–5939 (1990); and Stein et al., J. Neurosci., 10:1292–1298 (1990)) and in humans (Stein et al., New Engl. J. Med., 325:1123–1126 (1991); Khoury et al., Anesthesiology, 77:263–266 (1992); and Stein et al. Lancet, 342:321–324 (1993)).

A drawback to the widespread application of locally injected opioids for pain relief has been the fact that, although these peripheral analgesic effects may be elicited to some extent in inflamed tissue, these effects have not been elicited in non-inflamed tissue (C. Stein, Anesth. Anal., 76:182–191 (1993)). It is believed that one reason for this lack of opioid analgesic effect in non-inflamed tissue is the fact that opioid receptors on peripheral sensory nerves are not easily accessible due to a rather impermeable barrier sheath around those nerves, the so-called perineurium (Y. Olsson, Crit. Rev. Neurobiol., 5(3):265–311 (1990). This barrier is deficient in inflamed tissue and, therefore, the opioid receptors become easily accessible to opioid drugs under those circumstances. Therefore, it is important to find an analgesic, that when locally applied to normal tissue will elicit pain relief without the serious central opioid side effects.

The endothelial blood vessels in the brain (the so-called blood brain barrier, "BBB") can be artificially disrupted by hyperosmolar solutions (Olsson, Crit. Rev. Neurobiol., 5(3) :265–311 (1990)). Based on the known ultrastructural similarities between the perineurium and the BBB, the inventor performed experiments wherein such hyperosmolar solutions were injected into non-inflamed subcutaneous tissue of rats. The inventor found that these hyperosmolar solutions produced a leakage of the perineurium to analytes. This leakage was demonstrated by histochemical staining of peripheral nerves after subcutaneous injection of a marker substance (horseradish peroxidase) that normally does not easily penetrate into these nerves, but that did so after administration of hyperosmolar solutions. Further, mannitol and other hyperosmolar solutions, by themselves, are devoid of analgesic actions and (at the concentrations necessary to enhance local analgesic effects) are nontoxic in peripheral tissues.

Thus the inventor determined that the administration of extremely small, systemically inactive doses of opioids, opioid peptides (derivatives of the naturally occurring endorphins) or other local anesthetics result in a potent enhancement of the analgesic effects after local application in non-inflamed tissue when delivered in a hyperosmolar solution.

SUMMARY OF THE INVENTION

Accordingly, the present invention is directed to a method for enhancing the analgesic effects of opioids and other local anesthetics that act on peripheral nerves in tissues, and preferably in non-inflamed tissue, in a subject in need of such treatment, comprising administering a therapeutically effective amount of an opioid, an opioid peptide (derivatives of the naturally occurring endorphins), a local anesthetic or mixtures thereof (hereinafter sometimes collectively referred to as "agents, or active agents") in combination with a hyperosmolar solution and optionally other pharmaceutically acceptable carriers or diluents.

The significance of this invention lies in its applicability in a large variety of painful conditions in humans. Thus, the analgesic efficacy of locally and topically applied opiates and of other local anesthetics may be dramatically improved by the admixture of hyperosmolar solutions. Painful conditions amenable to such treatment include, but are not limited to, various injuries of the skin, such as burns, radiation, cuts, psoriasis; surgery, scars, infections; cancers; musculocutaneous and myofascial pain syndromes (e.g., low back pain); causalgia; sympathetically maintained pain; shingles; post-herpetic neuralgia; headache; and gastrointestinal, facial, urological, abdominal gynecological or postoperative pain.

An advantage of the methods of the present invention is pain relief by using extremely small doses of the active agent with hyperosmolar solutions and thereby foregoing all the untoward systemic side effects of opiates or local anesthetics.

(hatched bars) and effects of mannitol alone (open bars) in noninflamed paws. Values are means±SEM. Significance of differences is *, p<0.05; **, p<0.005 (n=7).

Figure 3:
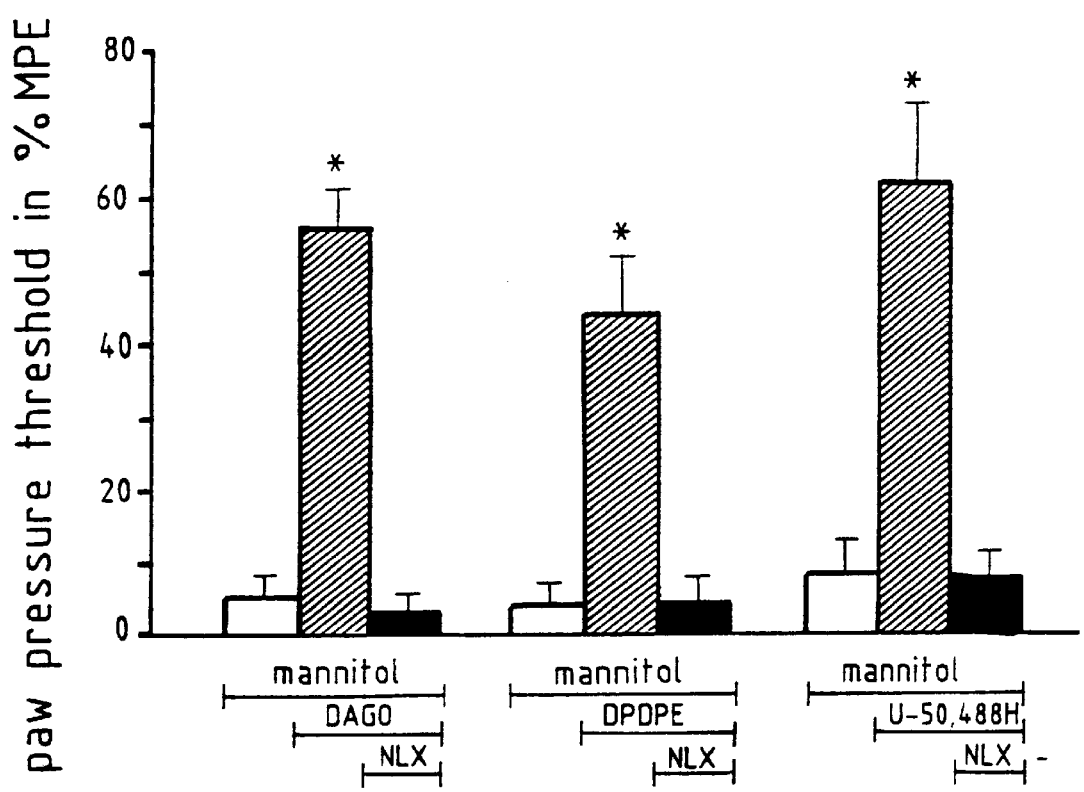

FIG. 3. Antinociceptive effects of mannitol (open bars), mannitol combined with opioid agonists (hatched bars) and the latter combination with naloxone (solid bars) in normal rats. Values are means±SEM. Significance of differences is *, p<0.05; **, p<0.005 (n=6–7).

Figure 4:
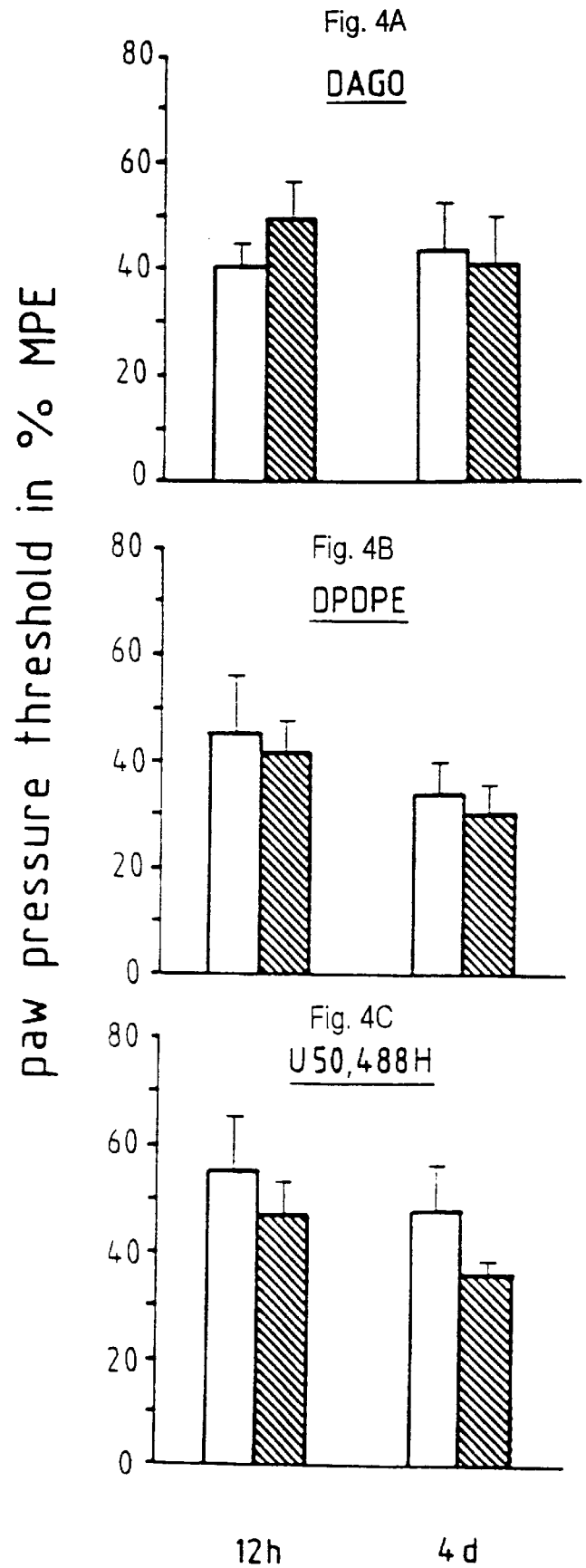

FIG. 4. Antinociceptive effects in noninflamed (open bars) and inflamed (hatched bars) paws after concomitant intraplantar injection of mannitol with either DAGO, DPDPE or U-50,488H. Separate groups were examined at 12 hr or 4 d after induction of inflammation. Values are means±SEM. significance of differences is *, p<0.05; **, p<0.005 (n=6–7).

Figure 5:
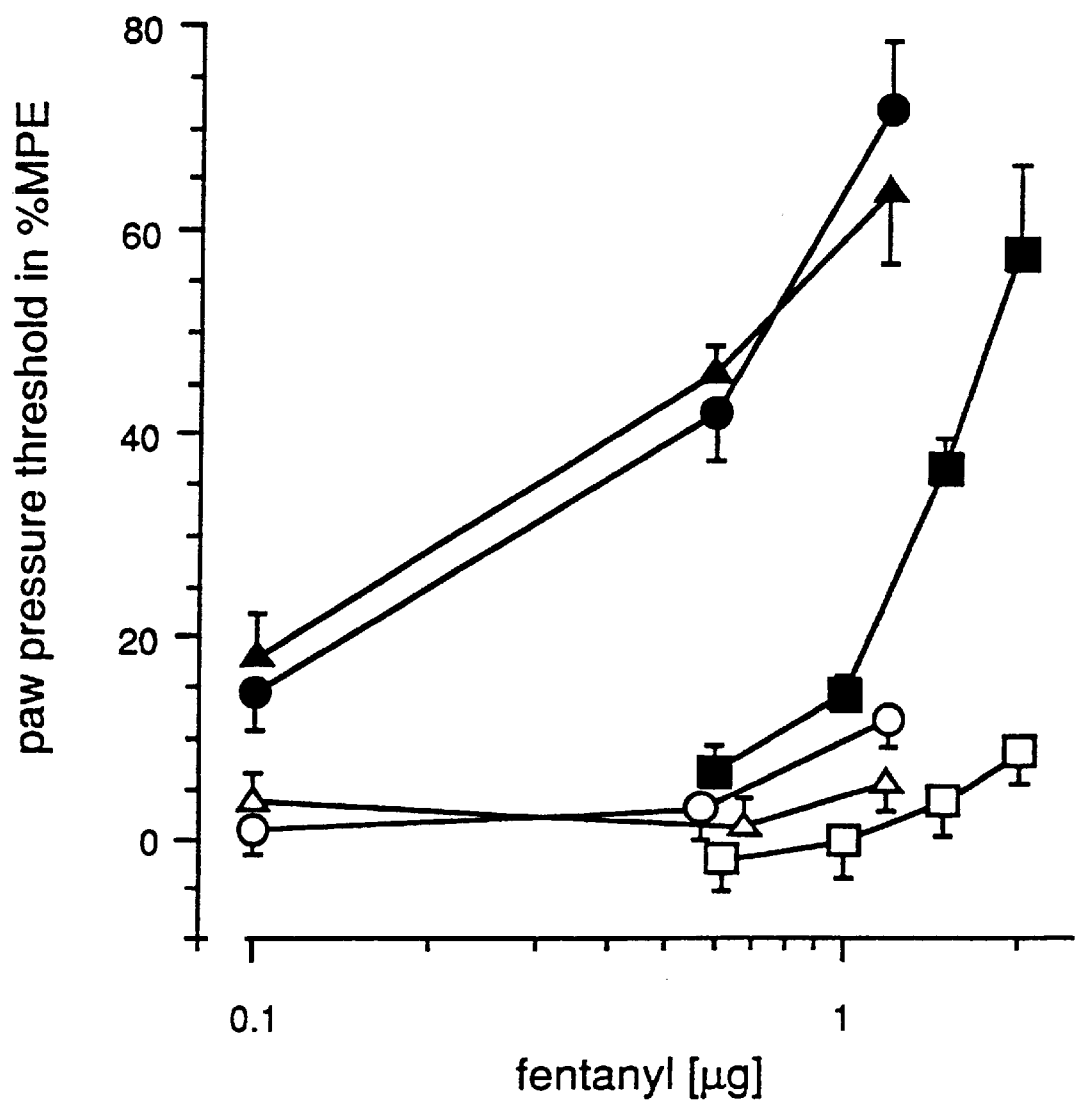

FIG. 5. PPT alterations (in % ME) after intraplantar administration of fentanyl (solid squares), saline (0.9%) (open squares and triangles) and of fentanyl-mannitol combinations (solid triangles) in normal rats and effects of intraplantar fentanyl in inflamed (solid circles) and noninflamed (open circles) paws of FCA-treated rats. Values are means±SEM.

DETAILED DESCRIPTION OF THE INVENTION

The term "opioids" or "opioid analgesics" as used herein and in the claims refers to compounds known to have an analgesic effect through the opioid receptors, and includes, but is not limited to morphine, cyclazocine, piperidine, piperazine, pyrrolidine, morphiceptin, meperidine, trifluadom, benzeneacetamine, diarylacteamide, benzomorphan, alkaloids, peptides, and pharmaceutically acceptable salts, prodrugs, or derivatives thereof.

The term "local anesthetic" as used herein and in the claims refers to compounds having an analgesic effect and includes, but is not limited to lidocaine, tetracaine, bupivacaine, pontocaine, prilocaine, etidocaine, and the like.

The term "hyperosmolar" refers to any solution or composition of solute above about 300 mOsm/l. Suitable solutes include, but are not limited to electrolytes, such as but not limited to sodium, potassium, chloride, magnesium and citrate; natural or synthetic amino acids known by those skilled in the art; saccharides, such as mannitol, sucrose, mannose, dextrose, glucose, dextran, starch, and the like. Preferred are solutions having 400 to 700 mOsm/L. More preferred are the solutions: 2–3% electrolyte solutions, 0.25–1M saccharide solutions. Specifically preferred are 2–3% NaCl, 0.25–1M mannitol.

As used herein and in the claims, the phrase "therapeutically effective amount" refers to that amount necessary to administer to a subject to achieve the desired analgesic effect, such amount being less than that amount necessary to elicit a systemic effect, and lacking in the concomitant adverse side effects normally associated with such opioids.

As used herein and in the claims, "Pharmaceutically acceptable salts, prodrugs and derivatives" refer to derivatives of the disclosed compounds that are modified by making acid or base salts, or by modifying functional groups present in the compounds in such a way that the modifications are cleaved, either in routine manipulation or in vivo in relation to the parent compounds. Examples include, but are not limited to, mineral or organic acid salts of basic residues such as amines; alkali or organic salts of acidic residues such as carboxylic acids; acetate, formate, sulphate and benzoate derivatives and the like.

The studies demonstrating that hyperosmolar solutions potently enhance peripheral opioid analgesic effects in tissue, particularly non-inflamed tissue were performed using generally accepted techniques known to those skilled in the art. For instance, the in vivo rat model was used as described in C. Stein, *Pharm. Biochem. Behavior*, 31:445–451 (1988), which is incorporated herein by reference in its entirety. This model has been extensively used, validated and shown to reliably measure analgesic effects of opiates and other analgesic drugs. Moreover, this model has proven highly predictive and correlative of therapeutically useful analgesic drug effects in humans in vivo (Stein et al., *New Enal. J. Med.*, 325:1123–1126 (1991)).

The present invention is further illustrated by the following non-limiting examples.

EXAMPLES

Experimental Protocols

A) Subjects. Experiments were performed in male Wistar rats (Sav Ivanovas, Kisslegg, Germany, and Charles River Laboratories) weighing 180–230 gm, housed individually in cages lined with sawdust. Standard rodent chow and water were available ad libitum. Room temperature and relative humidity were maintained at 22±0.5° C. and 40–50% respectively. A 12:12 hr (8 A.M./8 P.M.) light/dark cycle was used and testing was conducted in the light phase. animals were handled at least three times before any testing was performed.

B) Induction of inflammation. The inflammatory agent used was modified Freund's complete adjuvant (FCA), containing 0.1% heat-killed and dried *Mycobacterium butyricum* in 85% Marcol 52 and 15% Aracel A mannide monooleate emulsifier (Calbiochem, La Jolla, Calif.). Rats received an intraplantar injection of 0.15 ml of this suspension into the right hindpaw under brief ether anesthesia.

C) Compounds and their administration. The following commercially available compounds were used: (D-Ala 2, N-methyl-Phe 4, Gly-ol 5)-enkephalin ("DAGO"); (D-Pen 2,5)-enkephalin ("DPDPE"); trans-(±)-3,4-dichloro-N-methyl-N-(2-(1-pyrrolidinyl)cyclohexyl)-benzene-acetamide ("U-50,488H"); fentanyl-citrate; (−)-naloxone-HCl; D-(−)-mannitol ($C_6H_{14}O_6$, 182.17 gm/mol); horseradish peroxidase (HRP) type II; ether and halothane. Doses were calculated as the free base. U-50,488H, fentanyl, and naloxone were dissolved in sterile normal saline (0.9% NaCl); DAGO, DPDPE, and mannitol were dissolved in sterile water.

Intravenous (i.v.) injections were given in a volume of 0.2 ml via a 24-gauge indwelling plastic cannula into a tail vein under brief halothane anesthesia. Intraplantar (i.pl.) injections were given in a volume of 0.2 ml under brief ether anesthesia. Two minutes after termination of either anesthetic, the animals were fully awake and no behavioral anomalies were detected at any time. The mannitol solution had a pH of 6.79 and a temperature of 37° C. and was injected together with opioid agonists and/or antagonists over 20–30 sec.

D) In vivo Rat Model. Antinociceptive effects of drugs were evaluated using the generally accepted paw pressure test as described in C. Stein, *Pharm. Biochem. Behavior*, 31:445–451 (1988), which is incorporated herein by reference in its entirety. The animal was gently restrained under paper wadding and incremental pressure applied via a wedge-shaped blunt piston onto an area of 1.75 $mm^2$ of the dorsal surface of the hindpaw by means of a commercially available automated gauge. The pressure required to elicit paw withdrawal (PPT), was determined. A cutoff of 250 gm was employed. Three consecutive trials, separated by 10 sec., were conducted and the average calculated. The same procedure was then performed on the contralateral side; the sequence of sides was altered between subjects to preclude "order" effects. Separate groups of animals were used for each treatment. PPT's were assessed before injection (as a baseline) and were reevaluated 3–5, 10, and 20 min thereafter. The observer was blind to the experimental condition employed.

E) Data analysis. Two-sample comparisons were made using the generally accepted Wilcoxon test for dependent and the generally accepted Mann-Whitney U test for independent data. Multiple comparisons and post hoc tests were performed with the Friedman and Scheffe tests for dependent and the Kruskal-Wallis and Dunn tests for independent data. The Bonferroni correction was applied as appropriate (Zar, 1984). Dose-response curves were compared using a two-factor analysis of variance (ANOVA). Differences were considered significant if $p<0.05$ (two-tailed). The elevation in PPT was expressed as percentage of the maximum possible effect (% MPE) according to the following formula: (PPT postinjection-basal PPT): (250 gm-basal PPT). Mean values and the standard error of the mean (SEM) are given.

EXAMPLE 1

Figure 1:
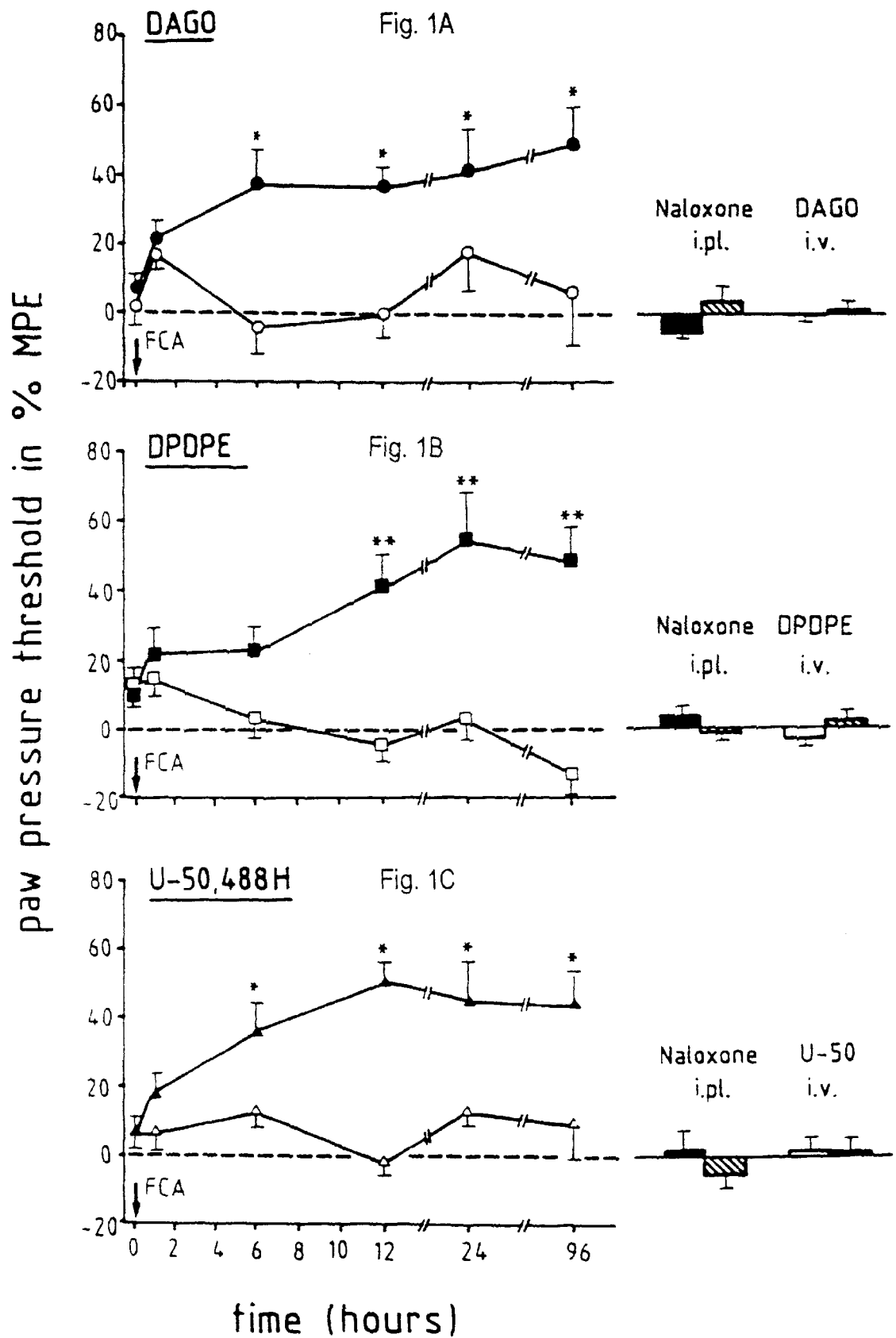
FIG. 1. PPT alterations (in % MPE) after intraplantar administration of 0.004 mg of DAGO, 0.04 mg of DPDPE, and 0.04 mg of U-50,488H before (0 hr) and 1, 6, 12, 24 and 96 hr after induction of inflammation in inflamed (solid symbols) and noninflamed (open symbols) paws. Effects of naloxone given concomitantly with the above agonists in inflamed (hatched bars) and noninflamed (solid bars) paws, and effects of intravenous administration of the above agonists in inflamed (hatched bars) and noninflamed (open bars) paws at 12 hr after FCA inoculation. Values are means±SEM. Significance of differences is *, $p<0.01$; **, $p<0.001$ (n=6–12).

The temporal evolution of peripheral opioid antinociception is shown in FIG. 1. The first significant elevation in PPT upon opioid administration was observed at 6 hr for DAGO and U-50,488H and at 12 hr for DPDPE (Kruskal-Wallis test, Dunn-test $p<0.01$) in inflamed paws. Thereafter PPT elevations remained stable (Kruskal-Wallis test, NS) (FIG. 1). In noninflamed paws neither agonist elicited significant changes in PPT (Kruskal-Wallis test, NS). Saline (0.9%) had no effect on PPT in either noninflamed or inflamed paws (not shown), neither had intravenous administration of agonists (U test, NS, compared to saline) (FIG. 1). The antinociceptive effects of all three opioid agonists in inflamed paws were completely reversible by concomitant administration of naloxone (U test, NS, compared to saline) (FIG. 1). Naloxone alone does not alter PPT at these doses.

Taken together, these data demonstrate a parallel appearance of inflammatory signs and peripheral opioid receptor-specific antinociceptive effects for all three agonists.

Experiments were performed to assess whether opioid-induced antinociception in inflamed paws could be mimicked in noninflamed tissue by concomitant administration of hyperosmotic mannitol. After baseline PPT measurement four groups of animals (n=6–8) without FCA pretreatment received 0.1 mL mannitol in different concentrations (0, 0.5, 1 or 2 mol/liter) together with 0.1 ml of sterile water (left paw) or DAGO (0.004 mg) (right paw). Three minutes later PPT were taken. To determine the time of maximum effect of mannitol, a group of normal rats (n=7) was injected with 0.5M mannitol into both hindpaws after determination of baseline PPT. Five minutes later, animals received DAGO (0.,004 mg) into the right paw. After another 5 min (i.e., 10 min after the mannitol injection) PPT were reevaluated. The results are shown in FIGS. 2.

Figure 2:
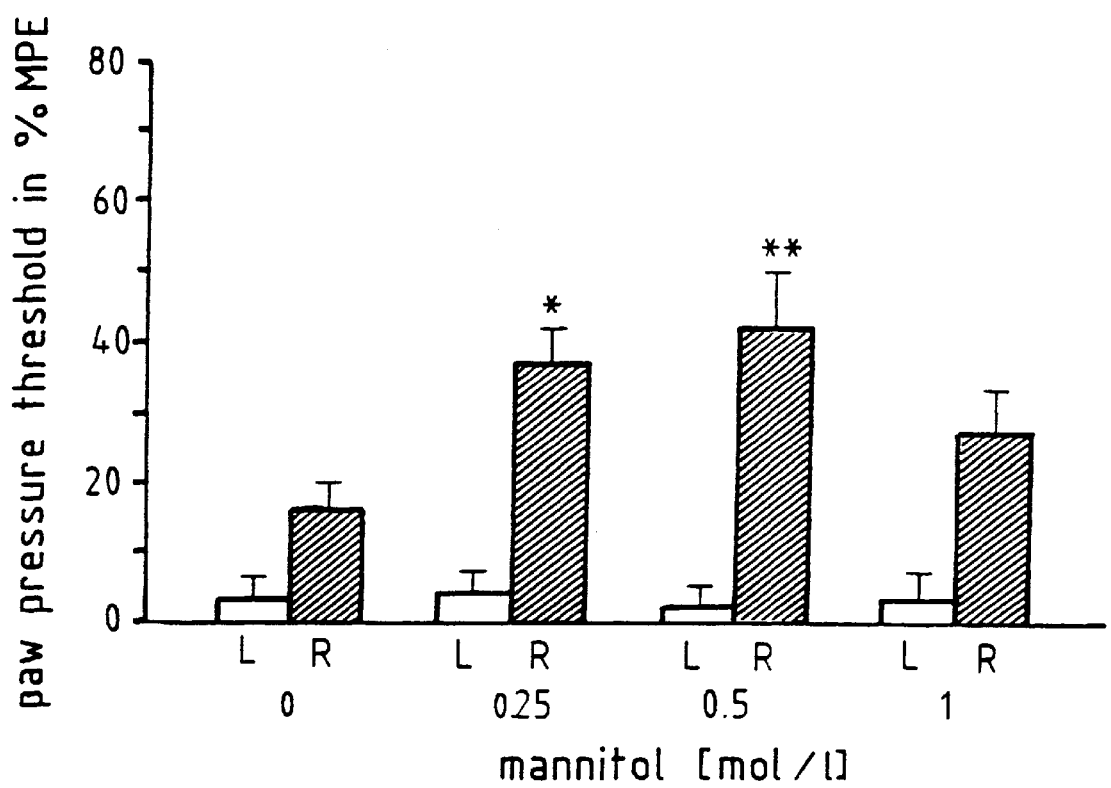
FIG. 2. Concentration-response relationship of antinociceptive effect of mannitol combined with DAGO (0.004 mg)

In normal rats, PPT elevations were significant following the addition of 0.25M mannitol and maximal after the addition of 0.5M mannitol to DAGO (Kruskal-Willis and Dunn test, $p<0.05$) and declined at higher concentrations (FIG. 2). No effect was seen in paws injected with mannitol alone (Kruskal-Willis test, NS) (see FIGS. 2, 3). When the mannitol injection preceded the DAGO administration by 5 min, no increase in PPT was detected (data not shown).

EXAMPLE 2

The opioid receptor specificity of the effects of mannitol-opioid combinations in noninflamed paws was tested in another experiment. Separate groups of normal rats (n=6–7) received mannitol, mannitol plus DAGO, DPDPE or U-50, 488H, or mannitol plus either agonist plus naloxone i.pl. To keep a total injection volume of 0.2 ml in the latter experiment, the following concentrations of drugs were applied: mannitol (0.1 ml, 1M); DAGO (0.004 mg/0.05 ml), naloxone (0.005 mg/0.05 ml); DPDPE (0.04 mg/0.05 ml), naloxone (0.04 mg/0.05 ml); U-50,488H (0.04 mg/0.05 ml), naloxone (0.005 mg/0.05). The results are shown in FIG. 3.

In normal rats, elevations of PPT similar to those described above were elicited by intraplantar mannitol-opioid combinations (FIG. 3). These effects were completely reversible by naloxone and mannitol alone was inactive (Kruskal-Wallis test, Dunn test, $p<0.05$) (FIG. 3). Taken together, these results indicate that, while a hyperosmolar mannitol solution itself has no effect on PPT, it allows opioid agonists to induce antinociception.

EXAMPLE 3

The effect of mannitol-opioid combinations in rats with inflamed paws was examined in the following experiment. At 12 hr and 4 d after FCA inoculation, respectively, six groups (n=6–7) received 1M mannitol together with either DAGO, DPDPE (0.04 mg), or U-50-488H (0.04 mg) into inflamed and noninflamed paws. The results are shown in FIG. 4.

All three opioid agonists, in combination with mannitol, produced PPT elevations in noninflamed paws that were comparable to those in inflamed paws at 12 hr and 4 d after inoculation (Wilcoxon test, NS) (FIG. 4). The addition of mannitol to opioids did not alter their antinociceptive effects in inflamed paws (U test, NS, compare FIG. 4 with FIG. 1).

EXAMPLE 4

The final experiment sought to examine whether a lipophilic opioid agonist produced peripheral antinociceptive effects in normal tissue, whether these could be further enhanced by mannitol and to compare these effects to those occurring in inflamed tissue. Seven separate groups of normal rats (n=6–7) received different doses of fentanyl (0.0001–0.002 mg/0.1 ml) with or without mannitol (0.1 ml, 1M) into one and normal saline into the contralateral hindpaw. Three groups of FCA-treated rats received different doses of fentanyl (0.0001–0.0012 mg/0.1 ml) into both hindpaws. PPT were assessed after 5 min. The results are shown in FIG. 5.

The results in FIG. 5 show that fentanyl produced dose-dependent elevations in the drug-treated but not in the contralateral saline-treated paw of normal rats. Mannitol significantly potentiated these effects ($p<0.005$) while saline-treated paw remained unaffected. In FCA-treated rats, significantly lower amounts ($p<0.005$) of fentanyl produced dose-dependent antinociceptive effects in inflamed paws while the same does range was ineffective in noninflamed paws. These effects were similar to those elicited by mannitol-fentanyl combinations in normal rats. The effective dose ranges of fentanyl are similar in inflamed and mannitol-treated paws ($p<0.05$, two factor ANOVA) and significantly lower ($p<0.005$, two factor ANOVA) than in normal paws. These results indicate that a lipophilic opioid in combination with hyperosmolar solutions produces peripherally mediated antinociception under normal conditions.

Examples 1–4 demonstrate that the antinociceptive effects of opioids in inflamed paws can be mimicked in noninflamed paws by concomitant application of hyperosmolar mannitol.

Thus, the present invention shows that peripheral opioid analgesic effects can be brought about in normal tissue as well as under inflammatory conditions, and the results demonstrate for the first time that the efficacy of both hydrophilic and lipophilic compounds can be improved dramatically by the concomitant modulation of perineurial permeability.

Dosage and Formulation

The methods of the present invention include local/topical application of compositions of opiates and/or other drugs with hyperosmolar solutions onto the external skin surface, injection into a wound or into various cavities (e.g., peritoneum, pleura, bladder, gastrointestinal tract). The methods of the present invention include administering the above compositions by any means that produces contact of the active agent with the agent's site of action in the body of a subject. They can be administered by any conventional means available for use in conjunction with pharmaceuticals, either as individual compositions or in a combination with other therapeutic agents. They can be administered alone, but will generally be administered with a pharmaceutical carrier selected on the basis of the chosen route of administration and standard pharmaceutical practice. The pharmaceutical compositions are suitable for parenteral, transdermal or transmucosal administration and may be in a dosage form as is well known to those skilled in the pharmaceutical art. The compositions may also be adapted for oral administration.

The term "parenteral" as used herein and in the claims includes subcutaneous, intramuscular, perineural, intrasternal, intraperitoneal, intrapleural, intraplantar, intraarticular injections, etc.

The appropriate dosage administered in any given case will, of course, vary depending upon known factors, such as the pharmacodynamic characteristics of the particular agent and its mode and route of administration; the age, general health, metabolism, weight of the subject and other factors which influence response to the agent; the nature and extent of symptoms; the kind of concurrent treatment; the frequency of treatment; and the effect desired. The amount of agent used will generally be an amount sufficient to elicit a local response, said amount insufficient to elicit a response if applied systemically.

Dosage forms (compositions suitable for administration) contain from about $10^{-12}$ milligrams to about 10 milligrams of active ingredient per unit. In these pharmaceutical compositions, the active ingredient will ordinarily be present in an amount of about 0.5–95% by weight based on the total weight of the composition.

The compositions can be applied locally/topically in different formulations such as sprays, solutions, aqueous suspensions, emulsions, gels, creams, solids, semi-solids etc.

The active ingredient may be administered in forms such as but not limited to, parenterally, in sterile liquid dosage forms, transdermally, via a patch mechanism or ointment and the like. They may also be administered orally in solid or semi-solid dosage forms, such as for example hard or soft-gelatin capsules, tablets and powders, or in liquid dosage forms, such as elixirs, syrups, disperse powders or granules, emulsions, and aqueous or oily suspensions.

The pharmaceutical compositions can be in the form of a sterile injectable preparation, for example, as a sterile injectable aqueous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example, a solution in 1,3-butane diol.

In general, water, a suitable oil, saline, aqueous dextrose (glucose), polysorbate and related sugar solutions and glycols such as propylene glycol or polyethylene glycols are also suitable carriers for parenteral solutions. Antioxidizing agents, such as but not limited to sodium bisulfite, sodium sulfite, or ascorbic acid, either alone or combined, are suitable stabilizing agents. Also used could be citric acid and its salts and sodium EDTA. In addition, parenteral solutions can contain preservatives, such as but not limited to benzalkonium chloride, methyl- or propyl-paraben, and chlorobutanol.

The pharmaceutical compositions of the present invention also include compositions for delivery across cutaneous or mucosal epithelia including transdermal, intranasal, sublingual, buccal, and rectal administration. Such compositions may be part of a transdermal device, patch, topical formulation, gel, etc., with appropriate excipients. Thus, the compounds of the present invention can be compounded with a penetration-enhancing agent such as 1-n-dodecylazacyclopentan-2-one or the other penetration-enhancing agents disclosed in U.S. Pat. Nos. 3,991,203 and 4,122,170 which are hereby incorporated by reference in their entirety to describe penetration-enhancing agents which can be included in the transdermal or intranasal compositions of this invention.

Suitable pharmaceutical carriers are described in *Remington's Pharmaceutical Sciences*, Mack Publishing Company, a standard reference text in this field, which is incorporated herein by reference in its entirety.

Compositions intended for oral use may be prepared according to any methods known to the art for the manufacture of pharmaceutical compositions and such compositions may contain one or more agents including sweetening agents, flavoring agents, coloring agents, and preserving agents in order to provide a pharmaceutically elegant and palatable preparation.

Tablets contain the active ingredient in admixture with non-toxic pharmaceutically acceptable excipients which are suitable for the manufacture of tablets. Such excipients may include, for example, inert diluents, such as calcium phosphate, calcium carbonate, sodium carbonate, sodium phosphate, or lactose; granulating disintegrating agents, for example maize starch or alginic acid; binding agents, such as starch, gelatin, or acacia; and lubricating agents, for example, magnesium stearate, stearic acids or talc. Compressed tablets may be uncoated or may be sugar coated or film coated by known techniques to mask any unpleasant taste and protect the tablet from the atmosphere, or enteric coated for selective disintegration and adsorption in the gastrointestinal tract.

Hard gelatin capsules or liquid filled soft gelatin capsules contain the active ingredient and insert powdered or liquid carriers, such as, but not limited to calcium carbonate, calcium phosphate, kaolin, lactose, lecithin starch, cellulose derivatives, magnesium stearate, stearic acid, arachis oil, liquid paraffin, olive oil and other diluents suitable for the manufacture of capsules. Both tablets and capsules can be manufactured as sustained release products to provide for continuous release of medication over a period of hours.

Aqueous suspensions contain the active compound in admixture with excipients suitable for the manufacture of aqueous suspensions. Such excipients are suspending agents, e.g., sodium carboxymethyl cellulose, methylcellulose, hydroxypropylmethylcellulose, sodium alginate, polyvinylpyrrolidone, gum tragacanth, and gum acadia; dispersing or wetting agents, such as a naturally occurring phosphatide, e.g., lecithin, or condensation products of an alkylene oxide with fatty acids, for example of polyoxyethylene stearate, or a condensation product of ethylene oxide with long chain aliphatic alcohols, e.g., heptadecaethyleneoxycetanol, or condensation products of ethylene oxide with partial esters derived from fatty acids and a hexitol, e.g., polyoxyethylene sorbitol monooleate, or a condensation product of ethylene oxide with partial esters derived from fatty acids and hexitol anhydrides, e.g., polyoxyethylene sorbitan monooleate. The aqueous suspensions can also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Disperse powders and granules suitable from preparation of an aqueous suspension by the addition of water provide the active ingredient in admixture with a dispersing or wetting agent, suspending agents and one or more preservatives. Suitable dispersing or wetting agents and suspending agents are exemplified by those already mentioned above. Additional excipients, for example, sweetening, flavoring, and coloring agents, can also be present.

Syrups and elixirs can be formulated with sweetening agents, such as glycerol, sorbitol or sucrose. Such formulations may also contain a demulcent, a preservative and flavoring and coloring agents.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art practice the claimed invention. Because the cited patents or publications may provide further useful information, these cited materials are hereby incorporated by reference in their entirety.

What is claimed is:

1. A method for enhancing the analgesic efficacy of a locally applied opioid analgesic or local anesthetic agent in a mammal having an impermeable perineurium barrier sheet about peripheral sensory nerves at the site of action of the locally applied opioid analgesic or local anesthetic agent, which comprises applying to said site an effective amount of the opioid analgesic or local anesthetic agent, or a pharmaceutically acceptable salt thereof, said analgesic or agent being dissolved in a hyperosmolar solution having an osmolality from above about 300 mOsm/L to 700 mOsm/L.

2. The method according to claim 1, wherein the opioid analgesic is an alkaloid.

3. The method according to claim 2, wherein the alkaloid is morphine.

4. The method according to claim 1, wherein the opioid analgesic is selected from the group consisting of cyclazocine, morphiceptin, meperidine, trifluadom, benzeneacetamine and benzomorphan.

5. The method according to claim 1, wherein the local anesthetic agent is selected from the group consisting of lidocaine, tetracaine, bupivaine, pontocaine, prilocaine and etidocaine.

6. The method according to claim 1, wherein said hyperosmolar solution is applied topically.

7. The method according to claim 1, wherein said hyperosmolar solution is applied parenterally.

8. The method according to claim 1, wherein said hyperosmolar solution is applied perineurally.

9. The method according to claim 1, wherein the hyperosmolar solution additionally contains glucose or sucrose.

10. The method according to claim 1, wherein the hyperosmolar solution additionally contains sodium chloride.

11. The method according to claim 1, where the hyperosmolar solution additionally contains amino acids.

12. The method according to claim 1, wherein the osmolality is from 400 to 700 mOsm/L.

* * * * *